United States Patent [19]
Gourley et al.

[11] Patent Number: 5,006,314
[45] Date of Patent: Apr. 9, 1991

[54] SENSOR AND METHOD FOR SENSING THE CONCENTRATION OF A COMPONENT IN A MEDIUM

[75] Inventors: Ted H. Gourley; Thomas P. Maxwell, both of Santa Ana; Thomas G. Hacker, Anaheim; William W. Miller, Santa Ana; Masao Yafuso, El Toro, all of Calif.

[73] Assignee: Minnesota Mining and Manufacturing Company, St. Paul, Minn.

[21] Appl. No.: 206,189

[22] Filed: Jun. 13, 1988

Related U.S. Application Data

[63] Continuation-in-part of Ser. No. 91,433, Aug. 31, 1987, abandoned, which is a continuation-in-part of Ser. No. 853,460, Apr. 18, 1986, abandoned, and a continuation-in-part of Ser. No. 917,913, Oct. 10, 1986, Pat. No. 4,798,738, and a continuation-in-part of Ser. No. 917,912, Oct. 10, 1986, Pat. No. 4,824,789, and a continuation-in-part of Ser. No. 49,844, May 15, 1987, Pat. No. 4,919,891.

[51] Int. Cl.⁵ ............................................. G01N 21/64
[52] U.S. Cl. ................................. 422/82.07; 128/642; 156/296; 250/227.14; 350/96.29; 356/39; 422/82.06; 427/2; 436/68; 436/165
[58] Field of Search .............. 422/58, 68, 82.06–82.11; 436/68, 165; 128/642; 250/227, 227.14; 350/96.29; 356/39, 402; 427/2; 156/296

[56] References Cited

U.S. PATENT DOCUMENTS

| | | |
|---|---|---|
| Re. 31,879 | 5/1985 | Lubbers et al. . |
| 2,780,611 | 2/1957 | Grotenhuis . |
| 3,335,715 | 8/1967 | Hugenholtz et al. . |
| 3,725,658 | 4/1973 | Stanley et al. . |
| 3,822,695 | 7/1974 | Takayama . |
| 3,864,019 | 2/1975 | Smolinsky et al. . |
| 3,866,599 | 2/1975 | Johnson . |
| 3,904,373 | 9/1975 | Harper . |
| 4,003,707 | 1/1977 | Lubbers et al. . |
| 4,194,877 | 3/1980 | Peterson . |
| 4,200,110 | 4/1980 | Peterson et al. . |
| 4,399,099 | 8/1983 | Buckles . |
| 4,476,870 | 10/1984 | Peterson et al. . |
| 4,487,206 | 12/1984 | Aagard . |
| 4,509,522 | 4/1985 | Mannuccia et al. . |
| 4,516,022 | 5/1985 | Lindgren . |
| 4,557,900 | 12/1985 | Heitzmann . |
| 4,560,248 | 12/1985 | Cramp et al. . |
| 4,568,518 | 2/1986 | Wolfbeis . |
| 4,577,109 | 3/1986 | Hirschfield . |
| 4,587,101 | 5/1986 | Marsoner et al. . |
| 4,600,310 | 7/1986 | Cramp et al. . |
| 4,639,594 | 1/1987 | Schoch et al. . |
| 4,657,736 | 4/1987 | Marsoner et al. . |
| 4,666,672 | 5/1987 | Miller et al. ............... 422/82.07 |
| 4,682,895 | 7/1987 | Costello . |
| 4,762,799 | 8/1988 | Seitz et al. ............... 422/58 |

FOREIGN PATENT DOCUMENTS

| | | |
|---|---|---|
| 0047094 | 8/1981 | European Pat. Off. . |
| 0105870 | 10/1983 | European Pat. Off. . |
| 2132348 | 7/1984 | United Kingdom . |

OTHER PUBLICATIONS

IEEE Transactions on Biomedical Engineering, John L. Gehrich, et al., vol. BME-33, No. 2, Feb. 1986.
Zhujun, et al, Analytica Chimica Acta, 160 (1984), pp. 305–309.

*Primary Examiner*—Jill Johnston
*Attorney, Agent, or Firm*—Gary L. Griswold; Walter N. Kirn; Dale E. Hulse

[57] ABSTRACT

An apparatus for sensing the concentration of a component such as oxygen in a medium such as blood. The apparatus includes an elongated signal transmitter and a sensing element at one end thereof. A substantially rigid sleeve is secured around such end to provide a pocket for the sensing element.

41 Claims, 1 Drawing Sheet

FIG. 1

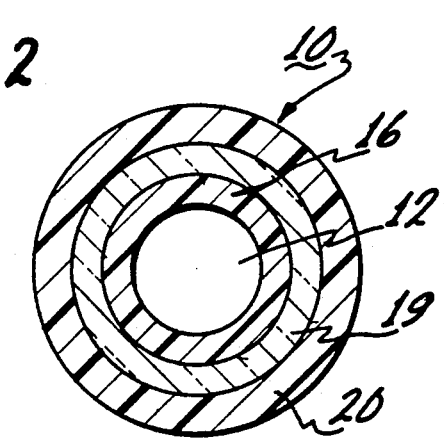
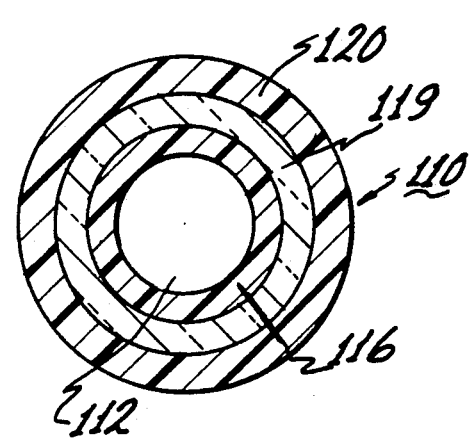

SENSOR AND METHOD FOR SENSING THE CONCENTRATION OF A COMPONENT IN A MEDIUM

RELATED APPLICATIONS

This application is a continuation in part of U.S. Pat. application Ser. No. 091,433, filed Aug. 31, 1987 (now abandoned), which in turn is a continuation-in-part of U.S. Pat. application Ser. No. 853,460, filed Apr. 18, 1986 (now abandoned); U.S. Pat. application Ser. No. 917,913, filed Oct. 10, 1986 (now U.S. Pat. No. 4,798,738); U.S Pat. application Ser. No. 917,912, filed Oct. 10, 1986 (now U.S. Pat. No. 4,824,789); and U.S. Pat. application Ser. No. 049,844, filed May 15, 1987 (now U.S. Pat. No. 4,919,891). Each of these applications is incorporated in its entirety by reference herein.

BACKGROUND OF THE INVENTION

The present invention relates to a sensing or measuring apparatus which includes a flexible signal transmitter, e.g., an optical fiber, and a flexible sensing element. More particularly, the invention relates to such an apparatus and method which involve means to reduce the detrimental effect of the flexibility of the signal transmitter and sensing element.

Sensors, e.g., optical sensors, are quite useful in systems to measure the concentration of a component in a medium. For example, optical sensors can be effectively employed for measuring or monitoring a given component in blood. Typical components measured by sensors include gases, such as oxygen and carbon dioxide, hydrogen ions (pH), electrolytes, glucose and the like.

Such sensors include an indicator, e.g., a fluorescent dye, which interacts with the component to be sensed or measured. Typically, the indicator, often in combination with a component permeable matrix, is a sensing element or sensor means and is placed on or adjacent a surface of a signal transmitter e.g., an optical fiber. The interaction between the indicator and the component to be sensed or measured is monitored utilizing signals carried by the signal transmitter.

The size of such sensors, which in certain instances are sufficiently small to be employed in vivo in the treatment of a medical patient, often results in the signal transmitter and sensing element being flexible. As used herein, an item is "flexible" if the application of a force perpendicular to the longitudinal axis of the item results in a displacement of the longitudinal axis. For example, a single optical fiber made of glass is normally flexible, as is the sensing element.

Although the signal transmitters and the sensing elements are typically flexible, such flexibility can cause substantial difficulties in obtaining accurate and consistent measurements. For example, such flexibility can result in the signal to be transmitted by the signal transmitter becoming distorted or otherwise not representative of the signal being provided by the indicator in the sensor. In addition, this flexibility may cause unwanted relative movement and separation of the signal transmitter and the indicator, which also may have a detrimental effect on the consistency and integrity of the signal being transmitted by the signal transmitter. In view of the size constraints imposed on such sensors, it is often not possible to avoid using flexible signal transmitters and sensing elements. However, it would clearly be advantageous to provide such a sensor in which the adverse effect of such flexibility is reduced. For example, it would be advantageous to reduce the probability of relative movement between the signal transmitter and the sensing element.

A number of U.S. Patents and an European Patent Publication have been considered in preparing this application.

Costello U.S. Pat. No. 4,682,895 discloses a probe which includes a light sending optical fiber, a light receiving optical fiber, a sample chamber filled with colorimetric substance, a tip support coating which extends proximally of the faces of both optical fibers, a protective sheath which terminates proximally of both of these faces and a semipermeable membrane. Costello teaches the tip support coating, and not the protective sheath, as providing a rigid protection for the tip of the probe. Also, Costello's system which involves two fibers (derived from a doubled-up single optical fiber) may be too bulky for certain applications.

Gudmunder, et al European Patent Publication No. 0,047,094 discloses an optical measuring system including a dual channel probe. Light is passed through the probe by one optical fiber to a fluid-solid interface to be measured which causes the interface to fluoresce or phosphoresce, and that resulting light is passed back through the probe by another optical fiber and analyzed. A plastic sheath surrounds middle portions (neither distal end nor proximal end) of the optical fibers, and is bonded to a flexible cable to join the probe to the cable and form a hermetic seal to prevent the ingress of contaminants. The sheath does not extend beyond either end of the optical fibers and therefore does not protect or support such ends.

Smolinsky, et al U.S. Pat. No. 3,864,019 discloses an unclad optical fiber firmly attached to a transparent substrate by photopolymerization of a transparent filter, e.g., cyclohexyl methacrylate, located between the unclad fiber and the substrate. Schoch, et al U.S. Pat. No. 4,639,594 discloses a fiberoptic probe which includes two optical fibers, a light source and two photomultipliers. Lindgren U.S. Pat. No. 4,516,020 discloses a system in which an optical fiber is surrounded by light transmitting glass or plastic. The system is used to detect undesired, light-producing events. Peterson, et al U.S. Pat. No. 4,200,100 discloses a probe including two optical fibers and a flexible protective sheath which extends well beyond the distal ends of the fibers. Peterson, et al U.S. Pat. No. 4,476,870 discloses a two optical fiber probe which includes a dye packing and a hydrophobic gas permeable porous envelope to isolate the dye packing from contamination. None of these systems is concerned with reducing the harmful effects of the flexibility of a sensing element and a signal transmitter, in particular a single optical fiber.

SUMMARY OF THE INVENTION

A new apparatus and method for sensing the presence, or concentration e.g., measuring the concentration, of a component in a medium has been discovered. In one broad aspect, the present system comprises sensor means including at least one indicator, preferably in a component permeable matrix; elongated signal means acting to transmit a signal from the sensor means, and sleeve means secured to the elongated signal means and extending distally of the distal end of the elongated signal means to at least partially define a pocket in which the sensor means is located. The sleeve means acts to reduce the possibility of relative movement between the sensor means and the distal end of the elongated signal means, i.e., relative to the possibility of such movement in a similar apparatus without the present sleeve means. The sleeve means preferably starts or commences proximally and terminates distally of the distal end of the elongated signal means. Further, the sleeve means is preferably more rigid than the elongated means.

The present apparatus simply and effectively reduces the adverse effect or effects often caused by the flexibility of the signal transmitter and/or of the sensor means. Reducing the apparent flexibility, or increasing the apparent stiffness, of the distal portion of the signal means, and preferably of the sensor means, reduces unwanted relative movement between this distal portion and the sensor means. This allows the signal means to transmit the signal from the sensor means more consistently or more reproducibly. This also reduces the chances of an undesirable change in the relative positions of the sensor means and the signal means because of this unwanted relative movement. More reliable component concentration measurements result.

The present apparatus may be utilized in an improved method for measuring the concentration of a component in a medium.

The present sleeve means extends out from the distal end of the signal means. Preferably, the sleeve means extends out from the distal end of the signal means a distance in the range of about 0.5 to about 2, more preferably about 0.8 to about 1.2, times the maximum transverse dimension, e.g., diameter, of such distal end.

The sleeve means may be of any suitable structure, orientation and configuration, and may be made of any suitable material of construction provided that it functions as described herein and has no substantial adverse effect on the other components of the present system or on the functioning of these components. The sleeve means preferably substantially surrounds the distal portion of the elongated signal means. This is advantageous since the surrounding sleeve conveniently protects the distal portion of the signal means and/or the sensor means from unwanted movement regardless of the direction of the force tending to cause this unwanted movement. Suitable materials from which the sleeve means can be constructed include, for example, polymeric materials such as polyimides and the like, and glass, with glass being an especially useful material of construction.

The sleeve means preferably further acts to increase the apparent stiffness and/or strength of the distal portion of the signal means and of the sensor means. That is, with the sleeve means in place, forces acting on this distal portion and on the sensor means preferably have less harmful effect, e.g., on the distal portion itself, on the sensor means itself, or on the relative position of the distal portion of the signal means and the sensor means, relative to such a system without the present sleeve means.

The presently useful indicators preferably function by modifying a source signal, e.g., from the signal means, in response to the presence of a certain component, e.g., oxygen, in medium, e.g., blood. Optical indicators are preferred for use in the present system. The preferred optical indicators are selected from the group consisting of luminescence, e.g., fluorescence indicators, absorbance indicators and mixtures thereof, with fluorescence indicators being especially preferred. Fluorescence indicators often include a dye which is sensitive or responsive to a component of interest. This dye, preferably in the component permeable matrix, can be placed on or adjacent the distal tip of the signal means, preferably an optical fiber, and exposed to the medium containing the component of interest. By monitoring the light signals from the dye tipped optical fiber, the concentration (partial pressure) of the component in the medium can be determined. Certain of the above-noted patent applications disclose various fluorescence indicators useful in the present invention.

If oxygen is the component of interest, the optical indicator is preferably selected from the group consisting of polynuclear aromatic compounds, derivatives of polynuclear aromatic compounds and mixtures thereof. More preferably, the optical indicator is a mixture of derivatives of polynuclear aromatic compounds, in particular tertiary butyl derivatives of decacyclene. Certain of these preferred optical indicators are described in the above-noted U.S. Pat. application Ser. No. 853,460 (now abandoned).

In addition to the preferred optical indicator, the sensor means preferably further includes a component permeable, polymeric matrix. By "component permeable" is meant that the substance in question, e.g., the polymeric matrix, is permeable to the component the concentration of which is to be determined or measured using the sensor. Any suitable polymeric matrix may be employed. The polymeric matrix should have no substantial adverse effect of the other components of the present system or on the functioning of such other components. Certain of the above-noted patent applications disclose suitable polymeric matrixes. The choice of polymeric matrix is dependent, for example, on the optical indicator being employed, the specific component of interest and the specific sensing application involved. Although various polymers can be employed for the polymeric matrix, it is important that the polymeric matrix have a high permeability to the component of interest so that the sensitivity of the optical indicator to the component of interest is adequate for the sensing application involved. One particularly useful class of polymeric matrixes is selected from the group consisting of silicone polymers and mixtures thereof. For example, the silicone polymer may be a dimethylsiloxane polymer, a diphenylsiloxane polymer, or a diphenyldimethylsiloxane copolymer. Of this group, dimethylsiloxane polymers are preferred because of their high component permeability. Other members of the homologous series which include the above-mentioned polymers might also be used and are included within the scope of this invention.

The polymeric matrix is preferably cross-linked to provide improved support and structure for the optical indicator included in the sensor means. The term "cross-linking" as used herein refers to a chemical reaction in which polymeric molecules are reacted with multi-functional, e.g., difunctional, compounds to join the polymeric molecules together by bridges or cross-links derived from the multi-functional compounds or cross-linking agents.

Various cross-linking agents and cross-linking catalysts may be employed to cross-link the polymeric matrix. Such agents and catalysts should have no substantial detrimental effect on the components of the present system or on the functioning of such components. The cross-linking reaction may be conducted in a conventional manner and, therefore, is not discussed in detail here.

As noted above, the present elongated signal means acts to transmit signals from the sensor means. The signals to be transmitted are influenced by or in response to the presence of the component of interest in the medium. This signal means is preferably further capable of delivering a source signal, e.g., excitation light, to the sensor. In one embodiment, the signal means comprises an optical fiber for (1) delivering excitation light to the sensor means so that the optical indicator in the sensor means can provide a signal which is influenced by or is in response to the component of interest; and (2) transmitting this signal from the sensor means. A light source, connected to the optical fiber, provides excitation light of the desired wavelength which is channeled down the fiber toward the sensor means. In response to this excitation light, the sensor means emits a light signal, e.g., a fluorescent light signal, which is dependent on the concentration of the component of interest to which the sensing means is exposed. This light signal or emission light is then channeled back up the same optical fiber to a light sensor for electrical readout and analysis of this light signal. Such analysis results in a determination of the concentration of the component of interest in the medium to which the sensing means is exposed. This procedure is similar to that described in Lubbers et al, U.S. Pat. No. Re. 31,879 and Heitzmann, U.S. Pat. No. 4,557,900, each of which is incorporated in its entirety herein by reference.

As noted above, the sleeve means is secured to the distal portion of the signal means. Preferably, the present apparatus further comprises adhesive means acting to adhesively secure the sleeve means to the signal means. For ease and consistency of manufacture, it is preferred that the adhesive means be curable by exposure to light energy, more preferably ultra-violet light energy. This feature is particularly useful in applications where the apparatus is small in size, e.g., sufficiently small to be useful in vivo in the treatment of a medical patient. The various components can be carefully situated to be in proper relation and position relative to each other without being concerned that the adhesive will cure or set up simply because of the passage of time. Once the components are properly in place, the adhesive in exposed to the required light energy and the adhesive is cured.

In one embodiment, the adhesive means is substantially component impermeable. By "component impermeable" is meant that the substance in question, e.g., the adhesive means, is impermeable to the component of interest.

Any suitable adhesive means may be used provided that such adhesive means function as described herein. This adhesive material should have no substantial detrimental effect on the other components of the present system or on the functioning of such components. The specific adhesive means chosen depends, for example, on the specific application involved. In one embodiment, the adhesive means includes additional optical indicator and acts to provide such additional optical indicator to the sensor means, e.g., over a period of time. The adhesive means is preferably a polymeric material. More preferably, the adhesive means is derived from a resin selected from the group consisting of epoxy resins and mixtures thereof. One particularly useful epoxy resin is sold under the tradename Dymax 20017 engineering adhesive by American Chemical & Engineering Company. This particularly useful epoxy resin is curable by ultra-violet light energy and is substantially impermeable to oxygen.

The present apparatus preferably further comprises an overcoating at least partially covering, and more preferably acting to protect, the sensor means. This overcoating preferably comprises a component permeable material and an effective amount of an opaque agent. The overcoating should be substantially insoluble in the medium. For example, if blood is the medium, the overcoating is preferably water insoluble. One particularly useful component permeable material for use in the overcoating is cross-linked cellulosic material. Such overcoatings are more fully described in the above-noted U.S. Pat. application Ser. No. 049,844 (now U.S. Pat. No. 4,919,891).

These and other aspects and advantages of the present invention are set forth in the following detailed description and claims, particularly when considered in conjunction with the accompanying drawings in which like parts bear like reference numerals.

BRIEF DESCRIPTION OF THE DRAWINGS

FIG. 1 is a side view, in cross section, of one embodiment of the present apparatus.

FIG. 2 is a cross-sectional view taken along line 2—2 of FIG. 1.

FIG. 3 is a side view, in cross-section, of another embodiment of the present apparatus.

FIG. 4 is a cross-sectional view taken along line 4—4 of FIG. 3.

DETAILED DESCRIPTION OF THE INVENTION

Referring now to FIGS. 1 and 2, a first sensor, shown generally at 10, includes an optical fiber 12 which has an optical surface 14, a adhesive layer 16, a sensing element 18, a glass sleeve 19 and an overcoating 20. Optical fiber 12 is connected to an appropriate light transmitting apparatus 13 which generates the excitation light. Optical fiber 12 is also connected to a light receiving apparatus 15 which receives and analyzes the emission light from sensing element 18, in a manner similar to that described in the above referenced Lubbers et al and Heitzmann patents.

Sensing element 18 is positioned directly up against and adjacent to optical surface 14 and down along the sides of the distal tip of optical fiber 12. Sensing element 18 includes an optical indicator, e.g., a fluorescent dye, dispersed in a polymeric matrix, which is permeable to the component to be sensed by first sensor 10.

Glass sleeve 19 completely surrounds the distal portion of optical fiber 12 and extends around the entire circumference of the major portion of sensing element 18, as evidence, for example, in FIGS. 1 and 2. Glass sleeve 19 extends out from optical surface 14 a distance equal to the diameter of optical surface 14. Glass sleeve 19 acts to increase the apparent stiffness or strength of, and to stabilize and at least partially immobilize, the distal portion of optical fiber 12 and sensing element 18. Glass sleeve 19 reduces the possibility of relative movement between the distal portion of optical fiber 12 and sensing element 18. In addition, glass sleeve 19 acts to partially define the space or pocket in which sensing element 18 is located. The increased apparent stiffness of the distal portion of optical fiber 12 and of sensing element 18 imposed by glass sleeve 19 results in more consistent signal transmission by optical fiber 12 and, therefore, more consistent component measurements.

Since glass sleeve 19 partially defines the space into which sensing element 18 is placed, the added apparent stiffness at the distal end of first sensor 10 reduces the chances of forces, e.g., perpendicular to the longitudinal axis of optical fiber 12, causing a physical separation between sensing element 18 and optical surface 14. This again leads to more consistent component concentration measurements.

Adhesive layer 16 surrounds the sides of optical fiber 12 a proximal distance away from optical surface 14 and acts to adhesively secure glass sleeve 19 to optical fiber 12. As shown in FIG. 1, adhesive layer 16 abuts sensing element 18 so that virtually no void space exists between adhesive layer 16 and sensing element 18. In other words, adhesive layer 16 is in direct contact with sensing element 18. Adhesive layer 16 is substantially component impermeable. In one modification, adhesive layer 16 includes an amount of the same optical indicator as is present in sensing element 18. The optical indicator in adhesive layer 16 is dispersed in the adhesive, which is preferably a polymeric adhesive. In this embodiment, the optical indicator in adhesive layer 16 is used to provide additional optical indicator to sensing element 18. This embodiment is more fully described in commonly assigned U.S. Pat. application Ser. No. 091,432, filed Aug. 31, 1987 (now U.S. Pat. No. 4,954,318). This application is incorporated in its entirety by reference herein.

Covering sensing element 18 and a portion of glass sleeve 19 is overcoating 20. Substantially the entire exposed area of sensing element 18 is covered by overcoating 20. Overcoating 20 includes an opaque agent dispersed in a component permeable matrix. This matrix is insoluble in the medium, e.g., blood, in which first optical sensor 10 is to be used. Because overcoating 20 completely covers the exposed area of sensing element 18, sensing element 18 has an opaque coating completely around its exposed area. This opaque coating optically isolates sensing element 18 from the optical environment outside of overcoating 20. Such overcoatings are more fully described in the above-noted U.S. Pat. application Ser. No. 049,844 (now U.S. Pat No. 4,919,891).

Although only one first optical sensor 10 is shown in FIGS. 1 and 2, first sensor 10 may normally be used in a probe which includes two or more of first sensors 10. A fiber body coating 22 is adhered to and completely surrounds optical fiber 12 away from the distal portion of optical fiber 12. Fiber body coating 22 is applied after first sensor 10 has been mechanically integrated with one or more other optical sensors into a probe. Each first sensor 10 in the probe is preferably structured to determine or measure a different component of interest. The probe comprising a plurality of first sensors 10 includes a probe tip overcoat, shown in FIG. 1 at 24. Probe tip overcoat 24 completely surrounds optical fiber 12 of all first sensors 10 making up the probe, forms a substantially smooth transition between optical fiber 12, glass sleeve 19 and overcoating 20, and, acts to substantially eliminate any pockets or voids between individual first sensors 10 of the probe. This is particularly important if the medium is blood since such pockets or voids could provide regions of stasis where blood could coagulate. Suitable materials for use as probe tip overcoat 24 are similar to materials useful for overcoating 20 which are more fully described in certain of the above-noted patent applications, in particular U.S. Pat. application Ser. No. 049,844 (now U.S. Pat. No. 4,919,891).

Another embodiment of the present invention is shown in FIGS. 3 and 4. In these figures, a second sensor, shown generally at 110, includes a second optical fiber 112, which has a second optical surface 114, a second adhesive layer 116, a second glass sleeve 119, a second overcoating 120, a second fiber coating 122 and a second probe tip overcoat 124. Second sensor 110 also includes a second sensing element 118 which abuts second optical surface 114, and a component permeable matrix layer 126 which includes a suitable opaque agent and abuts second sensing element 118. An appropriate second light transmitting apparatus 113 and a second light receiving apparatus 115 are connected to second optical fiber 112, and are structured and function in substantially the same way as light transmitting apparatus 13 and light receiving apparatus 15, respectively.

Second optical fiber 112, second optical surface 114, second adhesive layer 116, second sensing element 118, second glass sleeve 119, second overcoating 120, second fiber body coating 122 and second probe tip overcoat 124 of second optical sensor 110, except as indicated below, are structured and do function in much the same way as the corresponding elements, respectively, of first sensor 10.

Second sensor 110 differs from first sensor 10 in that opaque layer 126 is overlaid on second sensing element 118. Since second sensing element 118 is optically isolated by opaque layer 126, second overcoating 120 can be transparent, i.e., may not include an opaque agent. Alternatively, second overcoating 120 can also include an opaque agent.

First sensor 10 is preferably produced as follows. In the following description first sensor 10 is an oxygen sensor. Both the distal portion of optical fiber 12 and glass sleeve 19 are treated, e.g., with allyl trimethoxysilane coupling agent, so that both of these items are more responsive to the action of adhesive layer 16. After this treatment, adhesive layer (uncured) 16, e.g., made of an epoxy resin curable by ultraviolet light energy, is applied to the distal portion of optical fiber 12, and glass sleeve 19 is placed around the distal portion of optical fiber 12 in contact with uncured adhesive layer 16. After glass sleeve 19 is in place around the distal portion of optical fiber 12, uncured adhesive layer 16 is exposed to ultraviolet light energy to cure adhesive layer 16.

A cross-linking catalyst, e.g., chloroplatinic acid, is applied to the distal end of optical fiber 12 and glass sleeve 19. A mixture of tertiary butyl derivatives of decacyclene in combination with a silicone polymer and a cross-linking agent is introduced into the space at least partially defined by optical surface 12 and glass sleeve 19, and the silicone polymer is allowed to become cross-linked. Overcoating 20 is then applied and cross-linked. When first sensor 10 is included in a probe, probe tip overcoating 24 is applied and cross-linked. Fiber body coating 22 is then applied.

Second sensor 110 is preferably produced in much the same manner as described herein with regard to first sensor 10. One difference involves separate applications and cross-linking of second sensing means 118 and opaque layer 126.

Both first sensor 10 and second sensor 110 function, in general, as follows. This functioning is described with respect to first sensor 10, it being understood that, unless stated to the contrary, second sensor 110 functions in a similar manner. First sensor 10 is placed in a medium, e.g., blood, containing the component to be sensed/measured. As noted above, often first sensor 10 is included in a sensor probe which has a plurality of such first sensors 10, each preferably useful to measure a different component in the medium. For ease of illustration the functioning of only one first sensor 10 is discussed. However, it is understood that the use of such sensors in a sensor probe and the sensor probe itself is within the scope of the present invention.

Optical fiber 12 is used to provide excitation light from light transmitting apparatus 13 to sensing element 18 and to transmit a signal from sensing element 18 which varies in response to the concentration or partial pressure of the component of interest in the medium. This response signal is then received by light receiving apparatus 15 and analyzed or interpreted to determine the concentration or partial pressure of the component in the medium. First sensor 10 is used to continuously monitor the concentration or partial pressure of the component of interest in the medium.

The following representative, non-limiting examples illustrate certain aspects of the present invention.

EXAMPLE 1

A blood oxygen sensor, similar in construction to first sensor 10 is used to monitor the oxygen partial pressure in blood on a substantially continuous basis over a period of time.

In this blood oxygen sensor, glass sleeve 19 surrounds the distal portion of optical fiber 12 as shown in FIG. 1, and sensing element 18 is composed of an oxygen permeable, cross-linked dimethylsiloxane polymeric matrix with the optical indicator being a mixture of t-butyl derivatives of decacyclene. Overcoating 20 is composed of water insoluble, oxygen permeable, cross-linked cellulosic material in which an opaque agent, copper phthalocyanine, is dispersed. Adhesive layer 16 is composed of an epoxy resin which is cured by exposure to ultra-violet light energy and, dispersed therein, an amount of the above-noted mixture of t-butyl derivatives of decacyclene. This epoxy resin is sold under the tradename Dymax 20017 engineering adhesive, by American Chemical & Engineering Company. This entire blood oxygen sensor is sufficiently small to be suitable for use in vivo in the treatment of a human medical patient.

After a period of time in use, this blood oxygen sensor continues to provide consistent monitoring of the oxygen partial pressure of the blood.

EXAMPLE 2

A blood oxygen sensor, similar in construction to second sensor 110 is used to monitor the oxygen partial pressure in blood on a substantially continuous basis over a period of time.

In this blood oxygen sensor, second sensing element 118, second overcoating 120, and second adhesive layer 116 are composed of similar materials as sensing, element 18, overcoating 20 and adhesive layer 16, respectively, in Example 1. This entire blood oxygen sensor is sufficiently small to be suitable for use in vivo in the treatment of a human medical patient.

After a period of time in use, this blood oxygen sensor continues to provide consistent monitoring of the oxygen partial pressure of the blood.

While the present invention has been described with respect to various specific examples and embodiments, it is to be understood that the present invention is not limited thereto and that it can be variously practiced within the scope of the following claims.

What is claimed is:

1. An apparatus for sensing the concentration of a component in a medium comprising:
    sensor means including at least one indicator for providing a signal which varies in response to the concentration of a component in a medium;
    elongated signal means having a distal end at or near which said sensor means is located, said elongated signal means acting to transmit a signal from said sensor means;
    sleeve means more rigid than said elongated signal means, said sleeve means being secured to said elongated signal means and extending distally of said distal end of said elongated signal means to at least partially define a pocket in which said sensor means is located, said sleeve means acting to reduce the possibility of relative movement between said sensor means and said distal end of said elongated signal means; and
    overcoating means acting to at least partially cover said sensor means.

2. The apparatus of claim 1 wherein said sleeve means is substantially rigid.

3. The apparatus of claim 1 wherein said sleeve means extends distally of said distal end of said elongated signal means a distance in the range of about 0.5 to about 2 times the maximum transverse dimension of said distal end of said elongated signal means.

4. The apparatus of claim 3 wherein said sleeve means is substantially rigid.

5. In a method for measuring the concentration of a component in a medium involving transmitting a signal from a sensor which includes at least one indicator for providing a signal which varies in response to the presence of said component in said medium, the improvement which comprises utilizing the apparatus of claim 4.

6. The apparatus of claim 1 which further comprises adhesive means acting to adhesively secure said sleeve means to said elongated signal means.

7. The apparatus of claim 6 wherein said indicator is an optical indicator and said adhesive means includes additional optical indicator and acts to provide said additional optical indicator to said sensor means.

8. In a method for measuring the concentration of a component in a medium involving transmitting a signal from a sensor which includes at least one indicator for providing a signal which varies in response to the presence of said component in said medium, the improvement which comprises utilizing the apparatus of claim 6.

9. The apparatus of claim 1 wherein said elongated signal means is an optical fiber.

10. The apparatus of claim 9 wherein said optical fiber acts to transmit signals to and from said sensor means.

11. The apparatus of claim 10 which further comprises a light source for transmitting light signals through said optical fiber to said sensor means and a light receiver for receiving light signals from said sensor means through said optical fiber.

12. The apparatus of claim 1 wherein said sleeve means further acts to increase the apparent stiffness of at least one of said distal portion of said elongated signal means and said sensor means.

13. The apparatus of claim 12 wherein said sensor means further includes a component permeable, polymeric matrix.

14. The apparatus of claim 1 wherein said sleeve means is made of glass.

15. In a method for measuring the concentration of a component in a medium involving transmitting a signal from a sensor which includes at least one indicator for providing a signal which varies in response to the presence of said component in said medium, the improvement which comprises utilizing the apparatus of claim 14.

16. The apparatus of claim 1 wherein said indicator is an optical indicator.

17. The apparatus of claim 16 wherein said optical indicator is selected from the group consisting of fluorescence indicators.

18. The apparatus of claim 1 wherein said elongated signal means is further capable of delivering a source signal to said sensor means.

19. The apparatus of claim 18 wherein said elongated signal means is an optical fiber.

20. The apparatus of claim 1 wherein said pocket is substantially filled with component permeable material.

21. In a method for measuring the concentration of a component in a medium involving transmitting a signal from a sensor which includes at least one indicator for providing a signal which varies in response to the presence of said component in said medium, the improvement which comprises utilizing the apparatus of claim 1.

22. The method of claim 21 wherein said medium is an aqueous medium.

23. The method of claim 21 wherein said medium is blood.

24. The method of claim 21 wherein said component is selected from the group consisting of oxygen, carbon dioxide, hydrogen ions, electrolytes and glucose.

25. An apparatus for sensing the concentration of a component in a medium comprising:
    sensor means including at least one optical indicator for providing a signal which varies in response to the concentration of a component in a medium;
    elongated signal means having a distal end at or near which said sensor means is located, said elongated signal means acting to transmit a signal from said sensor means;
    sleeve means more rigid than said elongated signal means, said sleeve means being secured to said elongated signal means and extending distally of said distal end of said elongated signal means to at least partially define a pocket in which said sensor means is located, said sleeve means extending around the entire circumference of at least a portion of said sensor means, said sleeve means acting to reduce the possibility of relative movement between said sensor means and said distal end of said elongated signal means; and
    adhesive means acting to adhesively secure said sleeve means to said elongated signal means, said adhesive means including additional optical indicator and acting to provide said additional optical indicator to said sensor means.

26. The apparatus of claim 25 which further comprises overcoating means acting to at least partially cover said sensor means.

27. The apparatus of claim 26 wherein said overcoating means comprises a medium insoluble, component permeable polymeric material and an effective amount of an opaque agent.

28. The apparatus of claim 26 wherein said indicator is a fluorescence indicator and said overcoating means comprises a water insoluble, component permeable, cross-linked cellulosic material.

29. An apparatus for sensing the concentration of a component in a medium comprising:
    an optical fiber having a distal end;
    a sleeve member more rigid than said optical fiber, said sleeve member being secured to said optical fiber and extending distally of said distal end whereby said distal end and said sleeve member at least partially define a pocket;
    an optical indicator in said pocket for providing a signal which varies in response to the concentration of the component in the medium, said sleeve member extending around the entire circumference of at least a portion of said optical indicator, and said sleeve member acting to reduce the possibility of relative movement between said distal end of said optical fiber and said optical indicator; and
    overcoating means acting to at least partially cover said optical indicator.

30. The apparatus of claim 29 including an annular layer of adhesive on said distal portion of said optical fiber for securing said sleeve to said optical fiber, said annular layer terminating proximally of said distal end of said optical fiber.

31. The apparatus of claim 30 wherein said annular layer of adhesive cooperates with said optical fiber and said sleeve member to at least partially define said pocket, said pocket has an annular region surrounding said optical fiber closely adjacent said distal end of said optical fiber and at least some of said optical indicator is in said annular layer.

32. The apparatus of claim 29 wherein said sleeve member is substantially rigid.

33. The apparatus of claim 29 wherein said sleeve means extends distally of said distal end of said elongated signal means a distance in the range of about 0.5 to about 2 times the maximum transverse dimension of said distal end of said elongated signal means.

34. The apparatus of claim 29 wherein said pocket is substantially filled with component permeable material.

35. The apparatus of claim 29 wherein said optical fiber acts to transmit signals to and from said optical indicator.

36. In a method for measuring the concentration of a component in a medium involving transmitting a signal from a sensor which includes at least one indicator for providing a signal which varies in response to the presence of said component in said medium, the improvement which comprises utilizing the apparatus of claim 29.

37. An apparatus for sensing the concentration of a component in a medium comprising:
    elongated signal means having a distal end;
    sleeve means secured to said elongated signal means and extending distally of said distal end whereby said distal end and said sleeve means at least partially define a pocket which is substantially filled with component permeable material;
    sensor means in said pocket for providing a signal which varies in response to the concentration of the component in the medium, said sleeve means extending around the entire circumference of at least a portion of said sensor means, and said sleeve means acting to reduce the possibility of relative movement between said distal end of said elongated signal means and said sensor means; and overcoating means acting to at least partially cover said sensor means.

38. The apparatus of claim 37 wherein said elongated signal means is a single optical fiber and said distal end of said optical fiber is located in said sleeve means.

39. The apparatus of claim 37 wherein said elongated signal means comprises an optical fiber, said sleeve means comprises a sleeve member, and said sensor means comprises an optical indicator.

40. In a method for measuring the concentration of a component in a medium involving transmitting a signal from a sensor which includes at least one indicator for providing a signal which varies in response to the presence of said component in said medium, the improvement which comprises utilizing the apparatus of claim 37.

41. A method for producing an apparatus for sensing the concentration of a component in a medium, comprising the steps of:
 securing a sleeve member to an optical fiber having a distal end so that said sleeve member extends distally of said distal end and so that said sleeve member and said distal end at least partially define a pocket;
 placing an optical indicator in said pocket, said sleeve member extending around the entire circumference of at least a portion of said optical indicator; and
 placing an overcoating adjacent at least a portion of said optical indicator in said pocket.

* * * * *

UNITED STATES PATENT AND TRADEMARK OFFICE
CERTIFICATE OF CORRECTION

PATENT NO. : 5,006,314
DATED : April 9, 1991
INVENTOR(S) : Ted H. Gourley et al.

It is certified that error appears in the above-identified patent and that said Letters Patent is hereby corrected as shown below:

Col. 5, line 45, "in" should be --is--.
Col. 6, line 54, "evidence" should be --evidenced--.
Col. 9, line 58, after "sensing" delete the comma.
Col. 11, line 63, "26" should be --1--.
Col. 11, line 67, "26" should be --1--.
Col. 12, line 36 (claim 33, line 2), "means" should be --member--.

Signed and Sealed this

Eighth Day of September, 1992

Attest:

DOUGLAS B. COMER

Attesting Officer

Acting Commissioner of Patents and Trademarks